United States Patent [19]
Grob et al.

[11] Patent Number: 4,922,714
[45] Date of Patent: May 8, 1990

[54] DEVICE FOR MEASURING THE PARTICLE EMISSIONS OF AN INTERNAL COMBUSTION ENGINE

[75] Inventors: Ferdinand Grob, Besigheim; Ernst Linder, Muehlacker; Dieter Kienzler, Stuttgart; Roger Potschin, Marbach/Neckar; Heinz Stutzenberger, Vaihingen/Enz, all of Fed. Rep. of Germany

[73] Assignee: Robert Bosch GmbH, Stuttgart, Fed. Rep. of Germany

[21] Appl. No.: 254,623

[22] Filed: Oct. 7, 1988

[30] Foreign Application Priority Data

Nov. 23, 1987 [DE] Fed. Rep. of Germany ....... 3739622

[51] Int. Cl.⁵ ................................................ F01N 3/00
[52] U.S. Cl. ......................................... 60/276; 73/116
[58] Field of Search ............................. 73/116; 60/276

[56] References Cited

U.S. PATENT DOCUMENTS

| | | | |
|---|---|---|---|
| 3,362,387 | 1/1968 | Neumann | 60/276 |
| 3,384,746 | 5/1968 | Benz | 73/116 |
| 4,501,138 | 2/1985 | McCandless | 73/116 |

FOREIGN PATENT DOCUMENTS 1334472 10/1973 United Kingdom .

Primary Examiner—Douglas Hart
Attorney, Agent, or Firm—Edwin E. Greigg

[57] ABSTRACT

A device for measuring particle emissions of an internal combustion engine, in particular the soot concentration in the exhaust gas, has a signal transmission route. located between a transmitter and a receiver, which traverses a flow of exhaust gas carried in an exhaust gas tube of the engine. To avoid soiling of the active elements of the transmitter and receiver that would cause inaccuracies in measurement, the signal transmission route is embodied as a beam of light, which passes through two diametrically opposed openings in the wall of the exhaust tube. The light-admitting openings are each closed with a respective transparent disk. The disks are heatable and are heated to a temperature above the burnoff temperature of the particles. Appropriate light emitting and receiving elements are used in combination with appropriate heating and evaluation circuits which indicate the soot concentration and which control fuel input to change the soot concentration.

21 Claims, 2 Drawing Sheets

DEVICE FOR MEASURING THE PARTICLE EMISSIONS OF AN INTERNAL COMBUSTION ENGINE

BACKGROUND OF THE INVENTION

The invention relates to a device for measuring the particle emissions of an internal combustion engine, in particular for measuring the concentration of soot in the exhaust gas. Between a transmitter and a receiver, the device has a signal transmission route that traverses a flow of exhaust gas delivered to an exhaust gas tube.

Such devices are used in engines having fuel injection pumps. From the engine particle emissions, these devices derive a control variable for the fuel injection, with which variable the injection quantity at full load can be metered such that the maximum specified particle emission will not be exceeded (U.S. Pat. No. 3,744,461).

In a known device of this kind (British Pat. No. 1,334,472), an electrical detector is installed at the circumference of the exhaust tube carrying exhaust gas, and it receives a signal from an electrical transmitter that is also disposed on the circumference of the exhaust tube, directly opposite the detector. The intensity of the signal received by the detector—increases or decreases—depending on the type of detector whenever the concentration of soot in the flow of exhaust gas increases. The electrical output signal of the detector is amplified and forms a direct control signal for adjusting a valve. To preclude errors in measurement, caused by soot concentration at the detector and transmitter, as much as possible, a scavenging air curtain is disposed between the exhaust gas, on the one hand, and the active elements of the detector and transmitter, on the other. Nevertheless, deposits of soot on the active elements are unavoidable, if there is a long-term drift in the measured value.

OBJECT AND SUMMARY OF THE INVENTION

The apparatus according to the invention has an advantage that elements which are transparent prevent soot from being deposited directly on the active elements of the transmitter and the receiver, and a heating means that is provided assures the transparency of the elements, by burning off the soot deposited thereon. This prevents factors other than the soot concentration in the exhaust gas from perturbing the optical signal received and hence causing errors in measurement. The transparent elements may be in the form of sapphire or quartz disks or rods, which are sintered, glued or pressed into the ceramic elements. In individual cases, in particular when the disks or rods are flush with the exhaust tube, maintaining the transparency of the elements can be reinforced in that, in an exemplary embodiment of the invention, the elements are subjected to pulses of scavenging air on their surface facing into the flow of exhaust gas.

Substantial advantages are attained if, in a preferred embodiment of the invention, the optical transmitter and receiver are connected to one of the light-admitting openings via photoconductors, while a reflective surface is disposed behind the other light-admitting opening, with the transparent elements located between the photoconductor and the reflective surface, on one side, and the exhaust gas flow, on the other. In this way, the length of the beam of light penetrating the exhaust gas flow is doubled, with an unchanged diameter of the exhaust gas tube, so that without enlarging the exhaust gas tube, greater accuracy in measurement is attained.

The reflective surface can advantageously be embodied by a retroreflector, which is embodied by a suitably shaped sapphire or quartz element itself. A separate photoconductor leads from the optical transmitter and from the optical receiver to the one light-admitting opening. Both photoconductors discharge into a common end piece. The undesirable reflection of the emitted light, on the side oriented toward the photoconductor of the transmitter, can be reduced by embodying the transparent element as a double cone.

If the emitted light in divided by a reference diode into a measuring beam and a reference beam, in accordance with a further feature of the invention, the temperature drift, aging and other harmful influences of a light emitting diode (LED) embodying the light source for the light transmitted can be detected and compensated for in an evaluation circuit. If the reference diode is disposed in the receiver, a third photoconductor must couple the reference diode to the transmitter. If the reference diode is disposed in a side channel, downstream of the transmitter diode in the direction of transmission, then the third photoconductor is unnecessary.

In a further embodiment of the invention, the pulses of scavenging air mentioned above are advantageously furnished by a diaphragm pump driven by the surges in exhaust pressure. In this way, supplying the scavenging air requires no additional energy.

The invention will be better understood and further objects and advantages thereof will become more apparent from the ensuing detailed description of preferred embodiments taken in conjunction with the drawings.

DESCRIPTION OF THE PREFERRED EMBODIMENT

Figure 1:
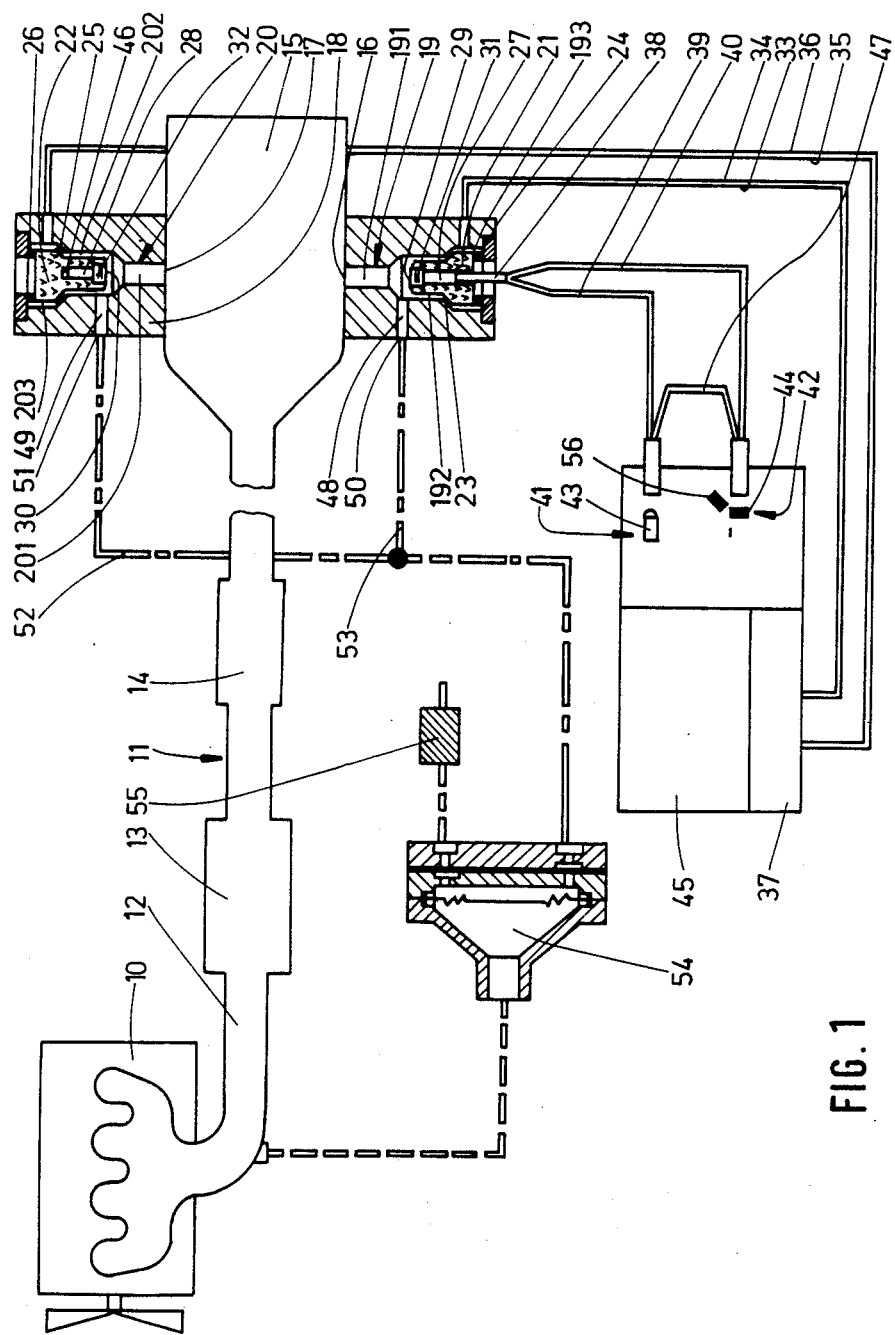
FIG. 1 shows a motor vehicle engine having an exhaust gas system and a device connected to it for measuring the soot concentration in the exhaust gas.

The drawing shows an internal combustion engine 10, in particular a Diesel engine, of a motor vehicle, serving as an example of an internal combustion engine, and the exhaust system 11 connected to the engine 10. The exhaust system comprises the exhaust gas guide tube 12, which includes one or two mufflers 13, 14 in series, and an exhaust gas end tube 15. The device for measuring the soot concentration in the flow of exhaust gas flowing through the end tube 15 is disposed on the end tube 15. To this end, the wall of the end tube 15 is provided with two diametrically opposed light-admitting openings 16, 17, and in the vicinity of the light-admitting openings 16, 17, the end tube 15 is surrounded in the vicinity by a connection ring 18, which includes oppositely disposed radial bores 19, 20 in alignment with the light-admitting openings 16, 17. The radial bores 19, 20 are embodied as stepped bores; the bore diameter of the individual bore sections 191–193 and 201–203 increases from the end tube 15 to the outer circumference of the connection ring 18. Separate ceramic bodies 21 and 22, respectively, adapted to the contours of the bore sections 192, 193 and 202, 203, are inserted into the two outer bores sections 192, 193 and 202, 203, respectively. The annular gap remaining between the ceramic bodies 21, 22 and the bore sections 192, 193 or 202, 203 is sealed off by ring seals 23, 24 and 25, 26, respectively, so that no exhaust gas can escape from the connection ring 18. Each ceramic body 21, 22 has an axial bore, which for the ceramic body 21 is embodied as a through bore 27 and for the ceramic body 22 is embodied as a blind bore 28. Both the through bore 27 and the blind bore 28 discharge at the face end of the respective ceramic body 21 and 22 oriented toward the end tube 15, where they are closed off by a transparent disk in the form of a sapphire disk 29, 30 sintered into the ceramic body 21 and 22. A platinum heating coil, schematically shown at 31 and 32, respectively, is disposed on the ceramic body 21 and 22 and is connected to two connection wires 33, 34 and 35, 36, respectively, which lead to a heating circuit 37. With these platinum heating coils 31, 32, the sapphire disks 29, 30 are heated to a temperature that is above the soot burnoff temperature, so that soot deposited on the sapphire disks 29, 30 is combusted without residue, so that the transparency of the sapphire disks 29, 30 remains assured.

A light conductor closure element 38 in which two light conductors 39, 40 are joined together is inserted into the through bore 27 of the ceramic body 21. One light conductor 39 leads to an optical transmitter 41 and the other light conductor 40 leads to an optical receiver 42. In the optical receiver 42, the light conductor 40 is optically coupled to a photodetector, in this case a simple photodiode 44. The transmitter 41 and the receiver 42 are connected to an evaluation circuit 45, which from the intensity of the transmitted light and the intensity of the received light calculates an absorption coefficient K or a coefficient of opacity T and compares it with rpm-dependent threshold values stored in a performance graph. Deviations from set-point values are used as control variables for correcting the quantity adjusting device of the fuel injection pump. The light emitted by the LED 43 is pulsed, so that the influence of stray light from the environment and the thermal radiation of the hot sapphire disks 29, 30 are compensated for. The wavelength of the light is preferably in the infrared range, since on the one hand IR diodes with a relatively high light yield are available, and on the other hand, the influence of the particle size in the exhaust gas on the results of measurement is lower with infrared light.

A reflective surface 46 in the form of a retroreflecting foil is disposed on the bottom of the blind bore 28 in the ceramic body 22 so that the light originating in the optical transmitter 41, which is introduced into the connection ring 18 via the light conductor 39, crosses through the end tube 15, is reflected at the reflective surface 46, crosses through the end tube 15 again, and then is delivered via the light conductor 40 to the optical receiver 42. Thus, the beam of light crosses through the flow of exhaust gas in the end tube 15 twice, and as a result the measurement route along which the soot concentration is detected is twice as long as the diameter of the end tube 15 of the exhaust system. A third light conductor 47 leads directly from the transmitter 41 to the receiver 42, where it acts upon a reference diode 56. By means of this arrangement, the light originating in the LED 43 is broken down into a measurement beam, transmitted via the light conductor 39, and a reference beam, transmitted via the light conductor 47. As a result, fluctuations in the intensity of the LED can be compensated for in a simple manner in the evaluation circuit 45.

Two axial bores 48, 49 extending at right angles to the radial bores 19, 20 are provided in the connection ring 18, each bore discharging in one of the radial bores 19, 20, in the vicinity of the second bore sections 192 and 202, respectively. The axial bores 48, 49 are provided with a scavenging air connection 50 and 51, respectivley, which communicate with a diaphragm pump 54 via respective scavenging air lines 52, 53. The diaphragm pump 54, the structure of which is known per se, communicates with the exhaust gas guide tube 12 and is driven by the pressure surges of the exhaust gas. The air aspirated via an air filter 55 is forced, in the form of pressure surges, via the scavenging air lines 52, 53 into the bore sections 192 and 202, where it acts upon the sapphire disks 29, 30. Thus, a supplementary cleaning effect upon the sapphire disks 29, 30 is attained. Via the bore sections 191 and 201, the scavenging air is delivered to the end tube 15, where it is removed along with the flow of exhaust gas.

The above-described device for measuring the concentration of soot in the engine exhaust gas functions as follows:

From the LED 43, light having a defined light intensity $\phi$ is emitted. The light intensity emerges from the closure piece 38 of the light conductor 38, passes through the light-admitting opening 16, crosses through the exhaust gas flow, and passes through the light-admitting opening 17 to strike the reflective surface 46. There, the beam of light is reflected, and it takes the same course in reverse back to the closure piece 38, from which it passes via the light conductor 40 to reach the photodiode 44 of the optical receiver After its double passage through the exhaust gas flow, the beam of light in the photodiode 44 is recorded as having an intensity $\phi_0$, if the exhaust gas is clean, or an intensity $\phi$, if an existing soot concentration makes the exhaust gas variably opaque. By Beer and Lambert's law, the intensity $\phi$ depends on the length of the measured route L, in this case twice the diameter of the exhaust gas tube; on the absorption properties K of the exhaust gas flow; and on the received intensity $\phi_0$ of the light if the exhaust gas is clean, in accordance with the following equation:

$$\phi = \phi_0 \cdot e^{-KL}.$$

In the evaluation circuit, the aborption coefficient K or the opacity T is calculated from the known received intensity $\phi_0$ of the beam of light when the exhaust gas is clean and from the light intensity $\phi$ measured at the photodiode 44, using the following equation:

$$T = 1 - \frac{\phi}{\phi_0} = 1 - e^{-KL}.$$

The opacity T is compared with rpm-dependent threshold values stored in a performance graph. Deviations in the actual values are compensated for by displacing the governor rod of the fuel injection pump, which varies the fuel injection quantity. Heating the sapphire disks 29, 30 and subjecting them to scavenging air protects the optical systems against soiling, which prevents inaccurate measurements.

Figure 2:
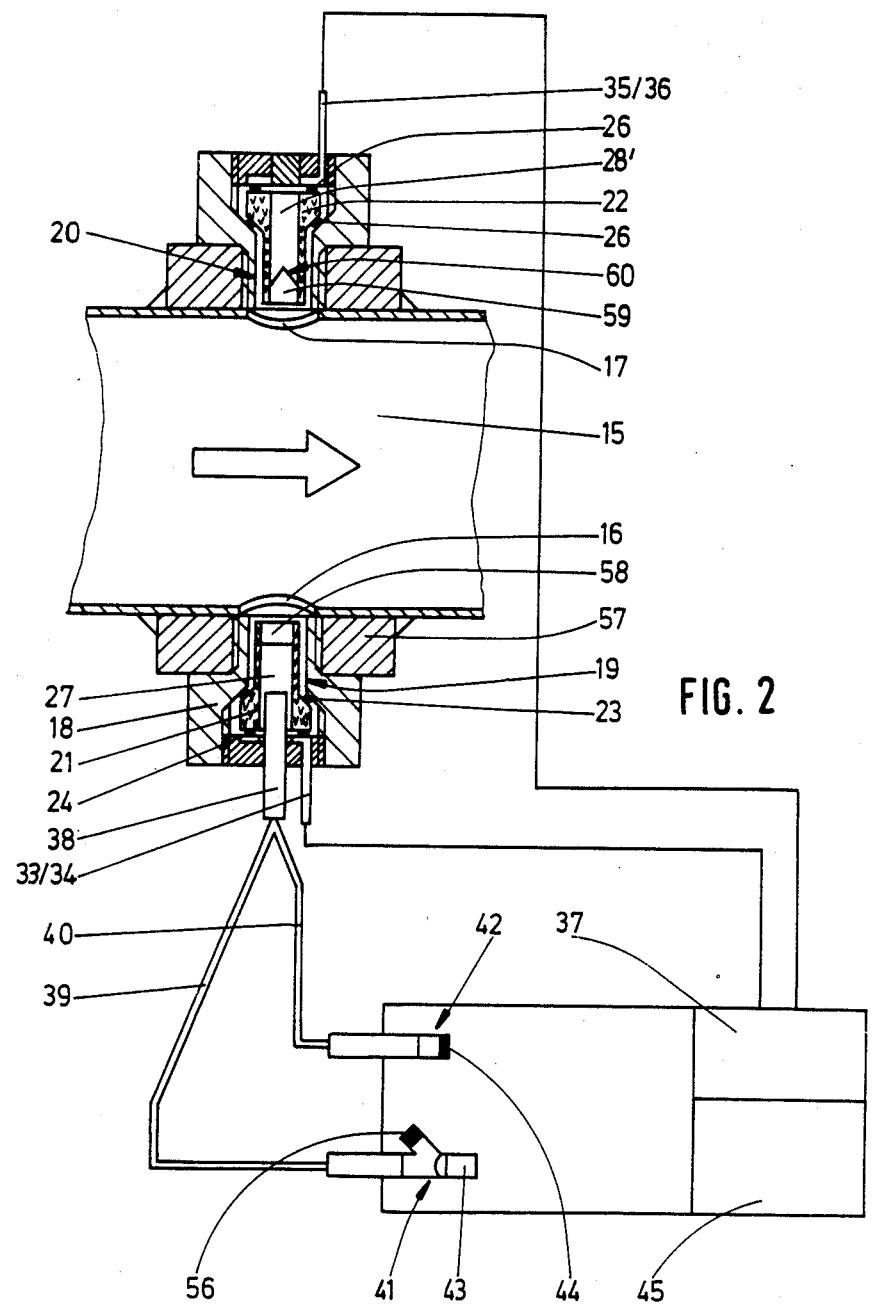
FIG. 2 is a detail showing an end tube of the exhaust gas system of FIG. 1, with a measuring device in accordance with a further embodiment of the invention.

The measuring device sketched in FIG. 2 is basically similar to that described above, except that some advantageous modifications have been made. The connection ring 18 is secured to the end tube 15 of the exhaust system by means of a ring holder or a welded-on plug 57 may be used. The ceramic bodies 21, 22 are inserted into the radial bores 19, 20 of the connection ring 18 in such a way that the transparent elements are flush with the light-admitting openings 16, 17 toward the interior of the end tube 15. The air scavenging operation is dispensed with entirely. The again heated, transparent bodies are in this case embodied as sapphire rods 58, 59, and the sapphire rod 58 disposed in the ceramic body 21 is a double cone, so as to avoid undesirable reflection on the side oriented toward the transmitter light conductor 39. The other sapphire rod 59, in the ceramic body 22, is embodied as a retroreflector 60, which performs the function of the reflective surface 46 of FIG. 1. To simplify manufacture, the axial bore in the ceramic body 22 is embodied not as a blind bore but rather as a through bore 28'.

The reference diode 56 is disposed not in the receiver 42 but in the transmitter 41, in a side channel, downstream in the transmission direction from the LED 43, so that once again it is acted upon by a portion of the transmitted light. The reference diode 56 is connected as before with the evaluation circuit 45. Its task is the same, but the third light conductor 47 present in FIG. 1 is unnecessary here.

Quartz rods or disks could also be used, instead of the sapphire rods 58, 59 or sapphire disks 29, 30.

The foregoing relates to preferred exemplary embodiments of the invention, it being understood that other variants and embodiments thereof are possible within the spirit and scope of the invention, the latter being defined by the appended claims.

What is claimed and desired to be secured by Letters Patent of the United States is:

1. A device for measuring the particle emission of an internal combustion engine, in particular for measuring a concentration of soot in an exhaust gas passing through an exhaust gas tube, said exhaust gas tube (15) includes oppositely disposed light admitting openings (16, 17) therein, means including oppositely disposed transparent bodies (29, 30, 58, 59) which close each of said openings (16, 17), a light source, a light receiver, means for directing a beam of light from said light source through said openings (16, 17), to traverse a flow of gas in said exhaust gas tube, means for directing said light beam that traverses said exhaust gas tube onto a said light receiver, and means for heating said oppositely disposed transparent bodies above a temperature at which any soot contaminants burn.

2. A device as defined by claim 1, which includes means (18, 57) that surround said openings (16, 17) that prevents escape of any exhaust gases along said exhaust gas tube, said means that surround said openings (16, 17) include radial bores directly opposite said openings (16, 17), a ceramic body (21, 22) positioned in each of said radial bores, and means for sealing each of said ceramic bodies to prevent escape of any soot or exhaust gases from said radial bores.

3. A device as defined by claim 2, in which each ceramic body (21, 22) has an axial bore (27, 28), which on an end oriented toward said light-admitting opening (16, 17) is closed off by said transparent bodies (29, 30; 58, 59).

4. A device as defined by claim 3, in which said axial axial bore (27) of one of said ceramic bodies (21) is a through bore, a light conductor closure element (38) inserted in said axial bore in said one ceramic body (21), a light conductor (39) and a light conductor (40) connected at one end to said light conductor closure element (38), said light conductor (39) conducts light from said light source (41) to said light conductor closure element (38) and said light conductor (40) conducts light from said light conductor closure element to said light receiver (42), a light reflector means (46) inserted in the axial bore (28) of said ceramic body (22), said reflector means (46) is preferably embodied by a retroreflector (60) which reflects light passing through said exhaust gas tube back to said light receiver.

5. A device as defined by claim 5, which includes a reference photodiode (56), which is exposed to a portion of the transmitted light which is compared with light received by said receiver.

6. A device as defined by claim 1, in which said light source is a light emitting diode (43), and said light receiver is a photodiode.

7. A device as defined by claim 2, in which said light source is a light emitting diode (43), and said light receiver is a photodiode.

8. A device as defined by claim 3, in which said light source is a light emitting diode (43), and said light receiver is a photodiode.

9. A device as defined by claim 4, in which said light source is a light emitting diode (43), and said light receiver is a photodiode.

10. A device as defined by claim 5, in which said light source is a light emitting diode (43), and said light receiver is a photodiode.

11. A device as defined by claim 6, in which said light source is a light emitting diode (43), and said light receiver is a photodiode.

12. A device as defined by claim 1, in which said transparent bodies are sapphire or quartz secured in said ceramic body (21, 22), and that a platinum heating coil (31, 32) is disposed on the ceramic body (21, 22) to heat said transparent bodies.

13. A device as defined by claim 1, in which said transparent bodies (29, 30) are exposed to scavenging air on a face oriented toward the exhaust gas tube.

14. A device as defined by claim 8, in which said scavenging air is delivered parallel to the face of said transparent bodies.

15. A device as defined by claim 8, which includes a diaphragm pump (54) driven by exhaust gas pressure surges provided for generating scavenging air.

16. A device as defined by claim 14, which includes a diaphragm pump (54) driven by exhaust gas pressure surges provided for generating scavenging air.

17. A device as defined by claim 3, which includes axial bores (48, 49) extending at right angles to said radial bores (19, 20) are provided in the connection element (18), each axial bore discharging into one of said radial bores and being provided with a scavenging air connection (50, 51).

18. A device as defined by claim 13, which includes axial bores (48, 49) extending at right angles to said radial bores (19, 20) are provided in the connection element (18), each axial bore discharging into one of said radial bores and being provided with a scavenging air connection (50, 51).

19. A device as defined by claim 14, which includes axial bores (48, 49) extending at right angles to said radial bores (19, 20) are provided in the connection element (18), each axial bore discharging into one of said radial bores and being provided with a scavenging air connection (50, 51).

20. A device as defined by claim 15, which includes axial bores (48, 49) extending at right angles to said radial bores (19, 20) are provided in the connection element (18), each axial bore discharging into one of said radial bores and being provided with a scavenging air connection (50, 51).

21. A device as defined by claim 16, which includes axial bores (48, 49) extending at right angles to said radial bores (19, 20) are provided in the connection element (18), each axial bore discharging into one of said radial bores and being provided with a scavenging air connection (50, 51).

* * * * *